United States Patent
Shur et al.

(10) Patent No.: US 7,321,109 B2
(45) Date of Patent: *Jan. 22, 2008

(54) CHARACTERISTIC AND/OR USE-BASED ELECTROMAGNETIC RADIATION GENERATION

(75) Inventors: Michael Shur, Latham, NY (US); Remigijus Gaska, Columbia, SC (US)

(73) Assignee: Sensor Electronics Technology, Inc., Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/746,172

(22) Filed: May 9, 2007

(65) Prior Publication Data

US 2007/0284508 A1    Dec. 13, 2007

Related U.S. Application Data

(63) Continuation of application No. 10/830,696, filed on Apr. 23, 2004, now Pat. No. 7,235,766.

(60) Provisional application No. 60/465,020, filed on Apr. 23, 2003.

(51) Int. Cl.
    *G01J 1/32*  (2006.01)
(52) U.S. Cl. .................. 250/205; 250/221; 315/155
(58) Field of Classification Search ............... 250/205, 250/221, 222.1, 225; 315/149, 291, 152–153, 315/155–159
    See application file for complete search history.

(56) References Cited

U.S. PATENT DOCUMENTS

| | | | |
|---|---|---|---|
| 5,340,974 A | 8/1994 | Zalewski | |
| 5,994,844 A | 11/1999 | Crawford et al. | |
| 6,043,476 A | 3/2000 | Tsai | |
| 6,072,281 A | 6/2000 | Ogawa | |
| 6,528,954 B1 | 3/2003 | Lys et al. | |
| 6,617,559 B1 | 9/2003 | Emery et al. | |
| 6,648,967 B2 | 11/2003 | Todt et al. | |
| 6,663,659 B2 | 12/2003 | McDaniel | |
| 7,235,766 B2 * | 6/2007 | Shur et al. ................... | 250/205 |
| 2005/0098713 A1 | 5/2005 | Holland | |

OTHER PUBLICATIONS

Brown, D. M., et al., "LED Backlight: Design, Fabrication, and Testing," Light-Emitting Diodes: Research, Manufacturing, and Applications IV, H. Walter Yao, et al., Editors, Proceedings of SPIE, vol. 3938, 2000, 8 pgs.

Hodapp, M. W., "Applications for High-Brightness Light-Emitting Diodes," Chapter 6, Semiconductors and Semimetals, vol. 48, Academic Press, 1997, pp. 227-229, 263-279.

Muthu, S., et al., "Red, Green, and Blue LEDs for White Light Illumination," IEEE Journal on Selected Topics in Quantum Electronics, vol. 8, No. 2, Mar./Apr. 2002, pp. 333-338.

Zukauskas, et al., "White Solid-State Lamps," Introduction to Solid-State Lighting, Chapter 6, John Wiley & Sons, 2003, pp. 117-132.

* cited by examiner

*Primary Examiner*—Patrick J. Lee
(74) *Attorney, Agent, or Firm*—Hoffman, Warnick & D'Alessandro, LLC

(57) ABSTRACT

Method and system for generating electromagnetic radiation wherein one or more attributes of the electromagnetic radiation are adjusted based on a characteristic of the object being illuminated. The object characteristic can be obtained based on a sensed property of the object and used to adjust the attribute(s) of the electromagnetic radiation accordingly.

20 Claims, 4 Drawing Sheets

CHARACTERISTIC AND/OR USE-BASED ELECTROMAGNETIC RADIATION GENERATION

REFERENCE TO PRIOR APPLICATIONS

The current application is a continuation application of U.S. patent application Ser. No. 10/830,696, filed on 23 Apr. 2004, now U.S. Pat. No. 7,235,766 and which claims the benefit of co-pending U.S. Provisional Application No. 60/465,020, filed on Apr. 23, 2003, both of which are hereby incorporated by reference.

BACKGROUND OF THE INVENTION

1. Technical Field

The invention relates generally to illumination devices, and more specifically, to an illumination device that includes one or more electromagnetic radiation sources that are adjustable based on a measured characteristic of an illuminated object.

2. Related Art

In illumination devices, two important characteristics are the efficiency with which it can generate electromagnetic radiation (e.g., radiant efficiency), and the efficacy of the generated electromagnetic radiation. In general, the radiant efficiency depends on the device power conversion performance, and has typically improved as technology matures. For example, to improve the radiant efficiency of an illumination device such as a light emitting diode (LED), one can seek to maximize both its internal quantum efficiency and its light extraction efficiency.

An acceptable efficacy of the electromagnetic radiation may be application dependent and/or based on one or more characteristics of an object being illuminated. In general, the efficacy of white light for a lighting application can be measured by its color rendering index (CRI). The CRI provides a quantitative measurement of how well the light renders objects of various colors. Based on the application, different values may be acceptable. Another measurement of the efficacy of white light is its spectral power distribution (SPD). The SPD measurement analyzes the relative power contributions from the various electromagnetic wavelengths that are combined to produce the electromagnetic radiation, e.g., the white light. In general, one can optimize the SPD of white light in order to obtain a higher CRI. In order to maintain white light having a desired SPD and/or CRI, several solutions incorporate feedback of the generated light.

However, the optimum SPD may vary based on one or more characteristics of the illuminated object(s). For example, an automobile headlamp should provide a very bright illumination of the road, while not blinding or creating excessive glare for the oncoming traffic. However, to date, no solution has been proposed that adjusts the SPD of electromagnetic radiation based on a characteristic of an illuminated object.

As a result, a need exists for a device that generates electromagnetic radiation that can be adjusted based on an illuminated object. In particular, a need exists a method and system for generating electromagnetic radiation that adjusts the electromagnetic radiation based on a measured characteristic of an illuminated object.

SUMMARY OF THE INVENTION

The invention provides a system and method of generating electromagnetic radiation. Specifically, under the present invention, electromagnetic radiation can be adjusted to include one or more desired attributes based on one or more characteristics of an object being illuminated by the electromagnetic radiation. In one embodiment, a feedback loop is incorporated to automatically obtain the characteristic(s) of the object and adjust the electromagnetic radiation accordingly. As a result, the invention provides a solution for illuminating an object with electromagnetic radiation having attribute(s) configured for the particular object being illuminated. In this manner, the electromagnetic radiation can be used in more diverse applications while providing electromagnetic radiation that illuminates details of the object more effectively.

A first aspect of the invention provides a method of generating electromagnetic radiation, the method comprising: obtaining a characteristic of an object to be illuminated; determining a desired spectral power distribution of the electromagnetic radiation based on the characteristic; generating the electromagnetic radiation having the desired spectral power distribution.

A second aspect of the invention provides a system for generating electromagnetic radiation, the system comprising: a measurement system for obtaining a characteristic of an object; an optimization system for determining a desired spectral power distribution of the electromagnetic radiation based on the characteristic; and an illumination system for generating the electromagnetic radiation having the desired spectral power distribution.

A third aspect of the invention provides a system for generating electromagnetic radiation, the system comprising: a measurement system for obtaining a characteristic of an object; an optimization system for determining a desired attribute of the electromagnetic radiation based on the characteristic, wherein the desired attribute comprises at least one of a spectral power distribution, an intensity time dependence, and a polarization; and an illumination system for generating the electromagnetic radiation having the desired attribute, wherein the illumination system includes an emitting element, and wherein the object is illuminated with the electromagnetic radiation.

The illustrative aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the invention provides a system and method of generating electromagnetic radiation. Specifically, under the present invention, electromagnetic radiation can be adjusted to include one or more desired attributes based on one or more characteristics of an object being illuminated by the electromagnetic radiation. In one embodiment, a feedback loop is incorporated to automatically obtain the characteristic(s) of the object and adjust the electromagnetic radiation accordingly. As a result, the invention provides a solution for illuminating an object with electromagnetic radiation having attribute(s) configured for the particular object being illuminated. In this manner, the electromagnetic radiation can be used in more diverse applications while providing electromagnetic radiation that illuminates details of the object more effectively.

Figure 1:
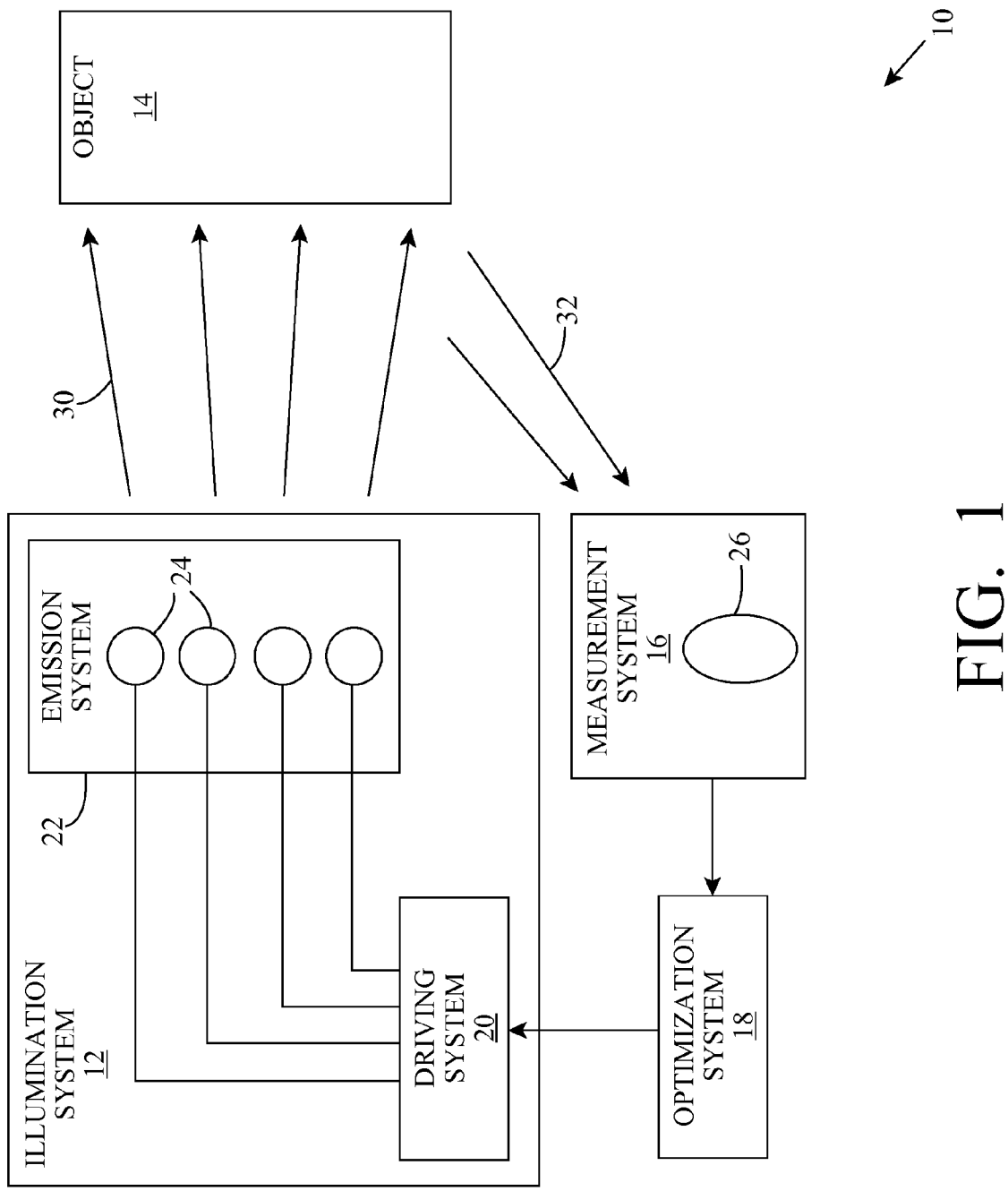
FIG. 1 shows an illustrative system for generating electromagnetic radiation.

Turning to the drawings, FIG. 1 shows an illustrative system 10 for generating electromagnetic radiation 30. In general, an illumination system 12 generates electromagnetic radiation 30 in order to illuminate object 14. Measurement system 16 obtains a characteristic of object 14, and an optimization system 18 determines a desired attribute of electromagnetic radiation 30 based on the characteristic. In response, illumination system 12 can adjust the generation of electromagnetic radiation 30 so that it includes the desired attribute. It is understood that throughout this discussion, the term "object" is used to generically refer to any combination of one or more physical items that are to be illuminated with electromagnetic radiation 30. To this extent, object 14 could be a single static item or be multiple items that change over time.

In any event, illumination system 12 is shown including a driving system 20 and an emission system 22. Driving system 20 can provide current, parameters, or the like to emission system 22 in order to generate electromagnetic radiation 30. Emission system 22 can include one or more emitting elements 24 that each emit electromagnetic radiation 30. To this extent, when a plurality of emitting elements 24 are present, the electromagnetic radiation emitted by each emitting element 24 can be mixed within illumination system 12 to generate electromagnetic radiation 30.

It is understood that electromagnetic radiation 30 can have any combination of one or more wavelengths. To this extent, electromagnetic radiation 30 can comprise one or more wavelengths within the visible spectrum (e.g., visible light). In this case, each of the one or more emitting elements 24 can comprise a light emitting diode (LED), an incandescent lamp, a fluorescent lamp, etc. Further, electromagnetic radiation 30 can comprise one or more wavelengths of various other spectra, including for example, the X-Ray spectrum, the infrared spectrum, the microwave spectrum, the millimeter spectrum, and the terahertz spectrum. As a result, each emitting element 24 can comprise any type of device capable of generating electromagnetic radiation 30 having any desired wavelength.

As previously mentioned, illumination system 12 can adjust electromagnetic radiation 30 to include a desired attribute. In one embodiment, driving system 20 can adjust operation of one or more emitting elements 24 to alter the resulting electromagnetic radiation 30. For example, driving system 20 can provide a driving current to each emitting element 24 (e.g., LED). In this case, driving system 20 can provide a distinct driving current to each emitting element 24 to allow for independent adjustment of each emitting element 24. However, it is understood that driving system 20 could provide the same driving current to a plurality of emitting elements 24 allowing for ready adjustment of the plurality of emitting elements 24 as a group. In order to adjust one or more emitting elements 24, driving system 20 can adjust a magnitude of the driving current and/or a pulse duration of the driving current as is known in the art. However, it is understood that driving system 20 can adjust emitting elements 24 in any known fashion. For example, driving system 20 could alter one or more parameters that alter the operation of an emitting element 24.

Illumination system 12 can adjust one or more of various attributes of electromagnetic radiation 30. For example, driving system 20 can adjust one or more of the wavelength, magnitude, etc., of the electromagnetic radiation generated by each emitting element 24. Further, illumination system 12 may be configured to emit electromagnetic radiation 30 for use in illuminating objects 14 for various applications. In each application, one or more characteristics of object 14 may differ, making a desired spectral power distribution of electromagnetic radiation 30 different for each application. In this case, illumination system 12 can adjust the spectral power distribution of electromagnetic radiation 30 based on one or more characteristics of object 14.

To this extent, system 10 is shown including a measurement system 16. Measurement system 16 can obtain one or characteristics of object(s) 14 using any solution. For example, a user (not shown) could enter in one or more characteristics for object 14 and/or select an application from which object 14 characteristics can be determined. Additionally, measurement system 16 can include one or more sensing elements 26 for sensing one or more properties of object 14. Based on the sensed property(ies), measurement system 16 can calculate the characteristic(s) of object 14.

The sensed property could be based on an emission from object 14, a reflection from object 14, or some combination thereof. For example, illumination system 12 can illuminate object 14 with electromagnetic radiation 30 that comprises a default attribute, e.g., a default spectral power distribution. Sensing element 26 can sense electromagnetic radiation 32 that has reflected off of object 14 to obtain one or more properties of object 14. Based on the reflected electromagnetic radiation 32, measurement system 16 can calculate the object 14 characteristic(s). However, it is understood that electromagnetic radiation 32 can comprise radiation that is emitted from object 14. In this case, illumination system 12 may not generate electromagnetic radiation 30 in order to obtain one or more properties of object 14. In an embodiment of the invention, measurement system 16 comprises a spectrometer detection unit that measures reflective and/or emitting characteristic(s) of object 14. To this extent, measurement system 16 can include a plurality of sensing elements 26 of the spectral power distribution.

Once obtained, measurement system 16 can provide the characteristic(s) of object 14 to optimization system 18. Optimization system 18 can determine the desired attribute of electromagnetic radiation 30 based on the characteristic(s). For example, a desired spectral power distribution of electromagnetic radiation 30 can be determined based on object 14 characteristic(s). Similarly, an intensity time dependence and/or a polarization for electromagnetic radiation 30 can be determined. It is understood that optimization system 18 can determine a single desired attribute (e.g., spectral power distribution) or multiple desired attributes (e.g., spectral power distribution, intensity time dependence, and polarization). The attribute(s) can be selected to provide high resolution, contrast, and the like for the illuminated object 14.

In any event, optimization system 18 can use any solution for determining the desired attribute that is now known or later developed. For example, when electromagnetic radiation 30 comprises visible light generated by one or more emitting elements 24, the following objective function could be used:

$$F(S_1, S_2, \ldots S_n, I_1, I_2, \ldots I_n) = \sum_i^m \sigma_i R_i$$

where $\sigma_i$ and $R_i$ are the weights and reflection coefficients of m spectral regions, and $S_i$ and $I_i$ are the respective spectral power distributions and intensities of n emitting elements 24 (e.g., light emitting diodes) of emission system 22. A computerized algorithm can be used to find the maximum of the objective function as is known in the art. The resulting values of $S_i$ and $I_i$ for each emitting element 24 can then be adjusted accordingly, so that emitting elements 24 generate electromagnetic radiation 30 having this maximum value.

Once determined, optimization system 18 can provide the one or more desired attributes to illumination system 12 (e.g., driving system 20) for use when generating electromagnetic radiation 30. To this extent, optimization system 18 can automatically update the desired attribute based on changing characteristic(s) of object 14. In this case, electromagnetic radiation 30 can be quickly adjusted to include the desired attribute(s) for illuminating object 14. As a result, a highly responsive system 10 for illuminating object 14 is provided.

Figure 2:
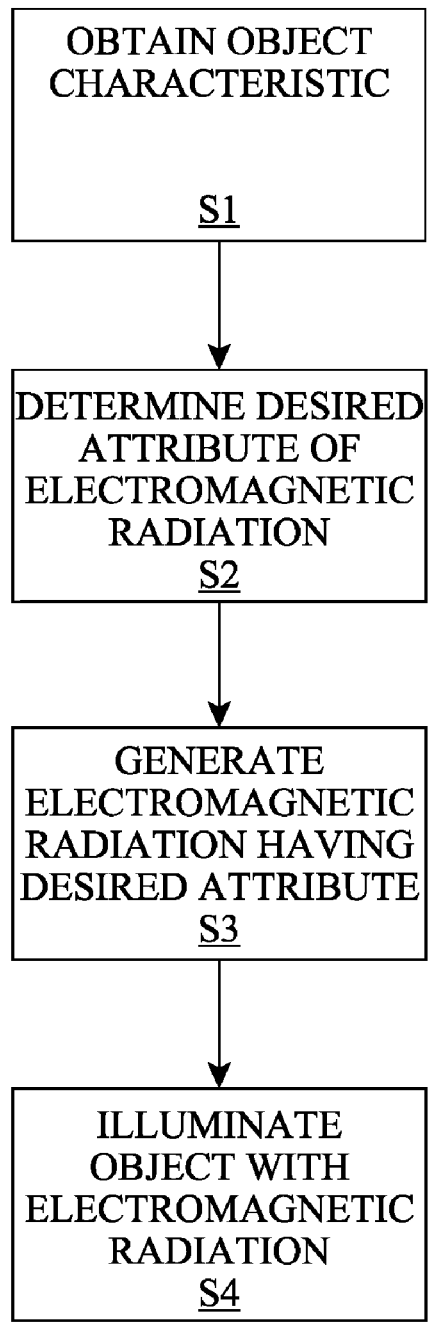
FIG. 2 shows illustrative method steps for generating electromagnetic radiation.
Figure 3:
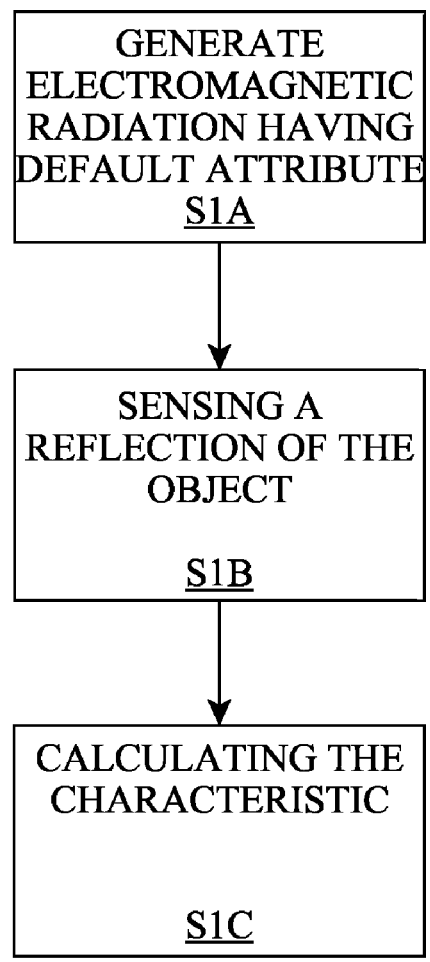
FIG. 3 shows illustrative method steps for obtaining an object characteristic.

FIG. 2 shows illustrative method steps for generating electromagnetic radiation 30 (FIG. 1). In step S1, one or more characteristics of object 14 (FIG. 1) are obtained by measurement system 16 (FIG. 1). FIG. 3 shows illustrative method steps that can be used to obtain characteristics of object 14. In step S1A, electromagnetic radiation 30 having one or more default attributes can be generated by illumination system 12. In step S1B, a reflection of the generated electromagnetic radiation 30 can be sensed by measurement system 16 to obtain one or more properties of object 14. In step S1C, the characteristic(s) of object 14 can be calculated by measurement system 16 based on the properties. Returning to FIG. 2, in step S2, a desired attribute of electromagnetic radiation 30 can be determined based on the characteristic(s) by optimization system 18 (FIG. 1).

Figure 4:
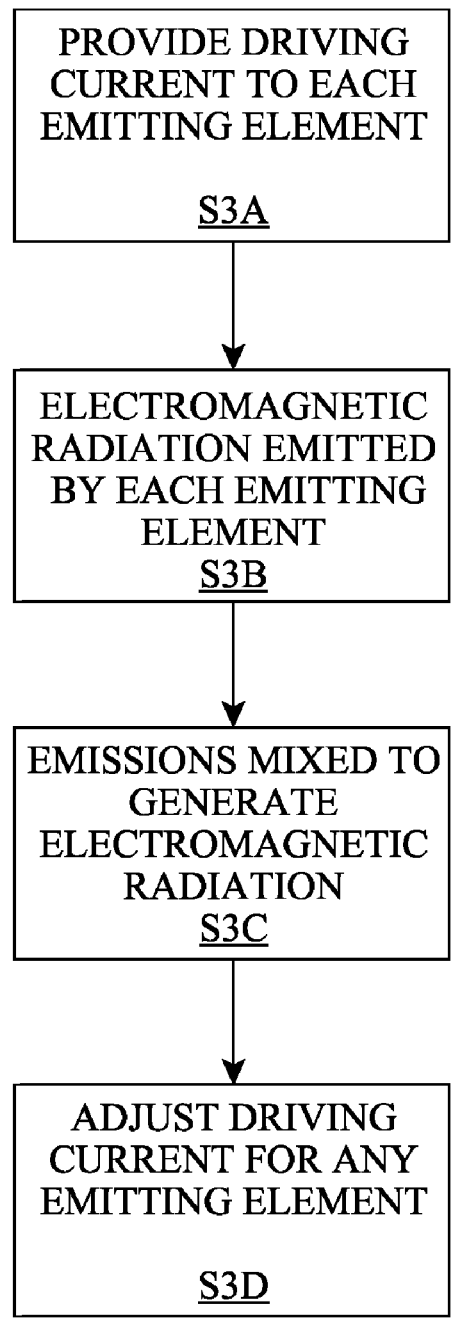
FIG. 4 shows illustrative method steps for generating electromagnetic radiation having a desired attribute.

In step S3, electromagnetic radiation 30 (FIG. 1) that includes the desired attribute can be generated by illumination system 12 (FIG. 1). To this extent, FIG. 4 shows illustrative method steps for generating electromagnetic radiation 30 according to one embodiment of the invention. In step S3A, a driving current is provided to each emitting element 24 (FIG. 1) by driving system 20 (FIG. 1). In step S3B, each emitting element 24 emits its own electromagnetic radiation. In step S3C, the emissions of emitting elements 24 are mixed to generate electromagnetic radiation 30. In step S3D, the driving current can be adjusted for one or more emitting elements 24 in order to obtain the desired attribute for electromagnetic radiation 30. Returning to FIG. 2, in step S4, the electromagnetic radiation 30 is directed to illuminate object 14 (FIG. 1).

Returning to FIG. 1, the invention can be incorporated into various applications. For example, system 10 could generate visible light for use in automobiles (headlights, brake lights, etc.), medical applications, spot illumination (e.g., surgical lamp), general lighting, etc. In one embodiment, illumination system 12 could generate light for automobile headlights, which could automatically switch from high to low beam and/or change a color temperature of the emitted light when measurement system 16 detects light emitted from oncoming traffic. To this extent, the adjustment could be programmed for a specific vision characteristic of the driver. In visible light applications, emitting elements 24 could comprise one or more of light emitting diodes (LEDs), conventional lamps, or some combination thereof.

Various other applications that do not use visible light are also possible. For example, in one embodiment of the invention, emission system 22 could include two emitting elements 24 that each comprises an ultraviolet LED that generates electromagnetic radiation having wavelengths of 260 nanometers and 360 nanometers, respectively. In this case, illumination system 12 could adjust the relative intensity for each emitting element 24 to enhance the signal to noise ratio when used for the detection of hazardous biological agents. Further, system 10 could be used to implement a radar having a variable spectral power distribution, a compact range radar, a phase array radar, etc. To this extent, in one embodiment of the invention, a radar detecting an incoming target could switch to generate electromagnetic radiation 30 having a shorter wavelength as the target approached, thereby improving the resolution of a target image. Still further, various types of semiconductor devices, power switching devices, etc., could be implemented using one or more embodiments of the invention. Additionally, it is understood that system 10 could be implemented alone or in combination with one or more other sources of electromagnetic radiation 30, including additional systems 10.

It is understood that one or more of the systems shown in system 10 (e.g., illumination system 12, measurement system 16, optimization system 18) could incorporate and/or be implemented using any combination of hardware and/or software. To this extent, one or more computing devices can be used, which can comprise a general purpose computing device, a specific use computing device, or some combination thereof. As is known in the art, each computing device can include a central processing unit (CPU), a memory, and an input/output (I/O) interface. The CPU performs operations based on computer program instructions and/or data stored in the memory, while the I/O interface provides an interface for transferring data between the computing device and one or more external devices, such as emitting elements 24, sensing element 26, and/or a user.

Any kind of computing device(s)—or other apparatus adapted for carrying out the methods described herein—is suited. A typical combination of hardware and software could be a general-purpose computer system with a computer program that, when loaded and executed, carries out the respective methods described herein. Alternatively, a specific use computer (e.g., a finite state machine), containing specialized hardware for carrying out one or more of the functional tasks of the invention, could be utilized. One or more of the various systems shown included therein can also be embedded in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of various embodiments of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of generating electromagnetic radiation, the method comprising:
   continually generating electromagnetic radiation to illuminate an object, the electromagnetic radiation initially having a set of default attributes; and
   repeatedly adjusting at least one attribute of the electromagnetic radiation based on a characteristic of the object, the adjusting including:
      determining a set of desired attributes of the electromagnetic radiation based on the characteristic and an efficacy of the electromagnetic radiation to provide at least one of: a high resolution or a high contrast for an object having the characteristic; and
      adjusting at least one attribute of the electromagnetic radiation emitted from an emitting element based on the set of desired attributes.

2. The method of claim 1, wherein the set of desired attributes includes a desired spectral power distribution of the electromagnetic radiation.

3. The method of claim 1, wherein the set of desired attributes includes a desired intensity time dependence of the electromagnetic radiation.

4. The method of claim 1, wherein the set of desired attributes includes a desired polarization of the electromagnetic radiation.

5. The method of claim 1, the adjusting the at least one attribute further including obtaining a distance of the object, wherein the determining is further based on the distance.

6. The method of claim 1, further comprising obtaining a use for the electromagnetic radiation, wherein the determining is further based on the use.

7. The method of claim 1, wherein the characteristic comprises a spectral power distribution of the object.

8. A system comprising:
   a system for generating electromagnetic radiation using a set of emitting elements;
   a system for determining a set of desired attributes of the electromagnetic radiation based on a characteristic of an object and an efficacy of the electromagnetic radiation to provide at least one of: a high resolution or a high contrast for an object having the characteristic; and
   a system for adjusting at least one attribute of the electromagnetic radiation emitted from an emitting element in the set of emitting elements based on the set of desired attributes.

9. The system of claim 8, wherein the set of desired attributes includes a desired spectral power distribution of the electromagnetic radiation.

10. The system of claim 8, wherein the set of desired attributes includes a desired intensity time dependence of the electromagnetic radiation.

11. The system of claim 8, wherein the set of desired attributes includes a desired polarization of the electromagnetic radiation.

12. The system of claim 8, further comprising a system for obtaining a distance of the object, wherein the set of desired attributes are further based on the distance and wherein the electromagnetic radiation comprises radio waves.

13. The system of claim 8, further comprising a system for obtaining a use for the electromagnetic radiation, wherein the set of desired attributes are further based on the use.

14. The system of claim 8, wherein the characteristic comprises a spectral power distribution of the object.

15. The system of claim 8, wherein the set of emitting elements includes:
   a first ultraviolet light emitting diode that generates electromagnetic radiation having a wavelength of approximately 260 nanometers; and
   a second ultraviolet light emitting diode that generates electromagnetic radiation having a wavelength of approximately 360 nanometers, wherein the electromagnetic radiation is used to detect a hazardous biological agent.

16. A lighting system comprising:
   a system for continually generating light using a set of emitting elements;
   a system for selecting one of a plurality of possible uses for the lighting system;
   a system for automatically obtaining a characteristic of an object to be illuminated by the light;
   a system for repeatedly determining a set of desired attributes of the electromagnetic radiation based on the characteristic of the object and the selected use; and
   a system for repeatedly adjusting at least one attribute of the electromagnetic radiation emitted from an emitting element in the set of emitting elements based on the set of desired attributes.

17. The system of claim 16, wherein the set of desired attributes are further based on an efficacy of the electromagnetic radiation to provide at least one of: a high resolution or a high contrast for an object having the characteristic.

18. The system of claim 16, wherein the set of desired attributes includes a desired spectral power distribution of the electromagnetic radiation.

19. The system of claim 16, wherein the characteristic comprises a spectral power distribution of the object.

20. The system of claim 16, wherein the plurality of possible uses include: automotive lighting, medical lighting, and general lighting.

* * * * *

UNITED STATES PATENT AND TRADEMARK OFFICE
CERTIFICATE OF CORRECTION

PATENT NO.       : 7,321,109 B2                    Page 1 of 1
APPLICATION NO.  : 11/746172
DATED            : January 22, 2008
INVENTOR(S)      : Michael Shur et al.

It is certified that error appears in the above-identified patent and that said Letters Patent is hereby corrected as shown below:

On the title page, in the Assignee, item 73, delete "Sensor Electronics Technology, Inc." and insert --Sensor Electronic Technology, Inc.--.

Signed and Sealed this
Twenty-fourth Day of December, 2013

Margaret A. Focarino
*Commissioner for Patents of the United States Patent and Trademark Office*